S. W. BURKE.

POCKET ATOMIZER.

APPLICATION FILED JUNE 30, 1916.

Reissued July 3, 1917. 14,325.

Witnesses

J. P. Lomlin

R. L. Parker.

S. W. Burke Inventor by C. A. Snow & Co.

Attorneys

UNITED STATES PATENT OFFICE.

SOLON W. BURKE, OF ARCHBOLD, OHIO.

POCKET-ATOMIZER.

14,325. Specification of Reissued Letters Patent. Reissued July 3, 1917.

Original No. 1,148,749, dated August 3, 1915, Serial No. 867,427, filed October 19, 1914. Application for reissue filed June 30, 1916. Serial No. 106,986.

*To all whom it may concern:*

Be it known that I, SOLON W. BURKE, a citizen of the United States, residing at Archbold, in the county of Fulton and State of Ohio, have invented a new and useful Pocket-Atomizer, of which the following is a specification.

The present invention relates to improvements in pocket atomizers, one object of the invention, being the provision of an atomizer of this character, adapted to fit within the vest pocket, and having means for permitting the fluid to be atomized to be drawn by inhalation through the nostrils and into the throat, or through the mouth instead of being forced by a bulb as is the usual practice with atomizers, thus producing a desirable easy application of the fluid without in any way injuring the membranes.

A further object of the present invention, is the provision of a novel construction of pocket atomizer, which is simple, durable and inexpensive in construction, and thoroughly efficient and practical in use.

With the foregoing and other objects in view which will appear as the description proceeds, the invention resides in the combination and arrangement of parts and in the details of construction hereinafter described and claimed, it being understood that changes in the precise embodiment of the invention herein disclosed can be made within the scope of what is claimed, without departing from the spirit of the invention.

In the drawings:—

Figure 1:
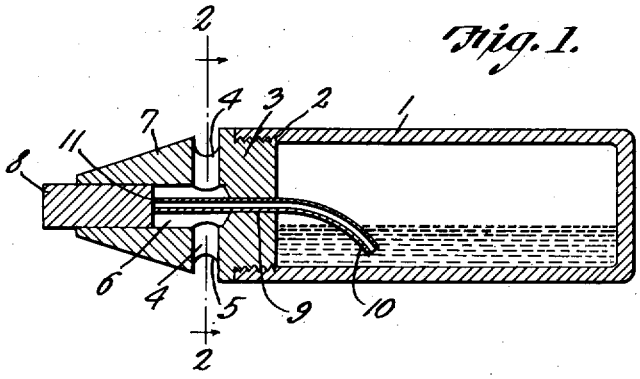
Figure 1 is a longitudinal sectional view through the complete atomizer.
Figure 2:
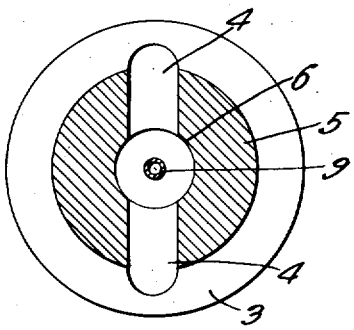
Fig. 2 is a section taken on line 2—2 of Fig. 1.
Figure 3:
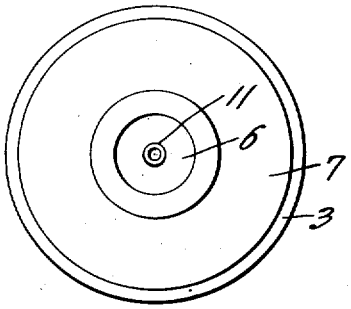
Fig. 3 is an end elevation of the frusto-conical end thereof.
Figure 4:
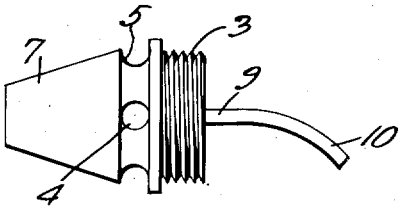
Fig. 4 is a side elevation of the frusto-conical member.

Referring to the drawings, the numeral 1 designates the vial or other container, which is interiorly screw threaded as at 2 for the reception of the plug 3. Carried by the plug 3 is a stem 5, which supports the frusto-conical member 7, which is chambered as at 6 and has in communication therewith, the diametrically disposed air admitting ports 4. The stopper 8 seals the chamber 6. This also provides a means for more readily directing the fluid to the affected parts.

Mounted concentrically through the stem 5 and the plug 3 is a tube 9, whose inner end is bent as at 10 so that the liquid within the vial will cover the same, when the present device is tilted for operation the outlet end 11 being disposed to project within the chamber 6 and beyond the bottom thereof so as to be sealed by the stopper 8 when the stopper is in the position as shown in Fig. 1.

It will be noted that the stem 5 provides a circumferential passage between the member 7 and the plug 3, so that air will be properly directed or admitted through the ports 4 and thus assist in the atomization of the fluid through the tube 9 as the operator either inserting the member 7 in the nostril or mouth may draw by inhalation.

Claims:

1. A pocket atomizer, including a container, a plug secured thereto, a stem carried by the plug, a frusto-conical member on the stem and having a chamber provided with a suction outlet for fluid and air, said stem having an air inlet port leading directly from the outer atmosphere to the chamber, and a fluid conducting tube communicating with the container and opening into the chamber through the plug and beyond the air inlet port.

2. A pocket atomizer, including a container, a plug connected thereto, a tapered member carried by the plug and provided with a chamber having a suction outlet through the outer end of said chamber, said chamber being provided with an air induction port adjacent to and in communication with the base portion of the chamber and in direct communication with the outer atmosphere, and a fluid conducting tube communicating with the container and extending through the plug and into the chamber beyond the induction port.

3. A pocket atomizer, including a container, a plug connected thereto, a tapered member carried by the plug and provided with a chamber having a suction outlet through the outer end of said member, said chamber being provided with an air induction port adjacent to and in communication with the base portion of the chamber and in direct communication with the outer atmosphere, a fluid conducting tube communicating with the container and extending through the plug and into the chamber beyond the induction port, and a stopper removably fitted in the outlet of the chamber to rest upon and seal one end of the tube.

4. A pocket atomizer including a container, a plug connected thereto, a frustoconical member carried by the plug and provided with a chamber having a suction outlet through the apex thereof, said chamber having an air induction port adjacent to and in communication with the base thereof and in direct communication with the outside atmosphere, and a tube having one terminal bent and disposed within the container while the opposite terminal is projected through the plug and within the chamber beyond the air induction port.

In testimony that I claim the foregoing as my own, I have hereto affixed my signature in the presence of two witnesses.

SOLON W. BURKE.

Witnesses:
DON ROSS,
MARCUS BOOKSH, Jr.